United States Patent [19]

Shah et al.

[11] 4,215,117

[45] Jul. 29, 1980

[54] STABLE PHARMACEUTICAL FORMULATIONS

[75] Inventors: Ashok C. Shah; Edward P. Strzelinski, both of Portage, Mich.

[73] Assignee: The Upjohn Company, Kalamazoo, Mich.

[21] Appl. No.: 909,924

[22] Filed: May 26, 1978

[51] Int. Cl.² .......................................... A61K 31/535
[52] U.S. Cl. ................................................. 424/248.4
[58] Field of Search ..................................... 424/248.4

[56] References Cited

U.S. PATENT DOCUMENTS 3,573,282   3/1971   Szmuszkovicz ............... 260/239.3 T

OTHER PUBLICATIONS

Chemical Abstracts, vol. 83 (1975), p. 136795j.
Chemical Abstracts, vol. 81 (1974), p. 111481z.
Chemical Abstracts, vol. 79 (1973), p. 145072r.

Primary Examiner—V. D. Turner
Attorney, Agent, or Firm—Robert A. Armitage; Hans L. Berneis

[57] ABSTRACT

Stable formulations of ketazolam containing 15 to 100 mg of ketazolam are prepared by admixing the ketazolam with either calcium lactate and a powdered edible vegetable fat or fatty oil, Sterotex®, or with calcium carboxymethylcellulose and Sterotex®.

4 Claims, No Drawings

STABLE PHARMACEUTICAL FORMULATIONS

BACKGROUND OF THE INVENTION

Field of the Invention

The compound, 11-chloro-8,12β-dihydro-2,8-dimethyl-12b-phenyl-4H-[1,3]oxazino[3,2-d][1,4]benzodiazepine-4,7(6H)-dione, generic name ketazolam, U.S. Pat. No. 3,573,282, is an excellent tranquilizer and antianxiety agent which can not only be used for the treatment of the mildly anxious patients, but also for the severely anxious institutionalized patients and for the treatment of alcoholics. Ketazolam has the chemical structure:

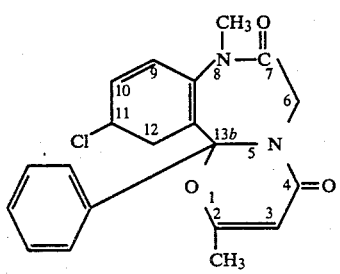

This compound is found to be reasonably chemically stable when pure but in the pharmaceutically most convenient formulation, i.e., capsules, which contain the active product with conventional excipients, the stability of ketazolan is greatly reduced.

The present invention is directed to improved formulations of ketazolam which were found to overcome the difficulty encountered by the relative instability of older formulations. Sterotex ®, an edible vegetable oil/fat, is used with either calcium lactate or calcium carboxymethylcellulose as the only excipients which provide reasonable stability to the ketazolam in formulations.

A typical set of data comparing the stability of pure ketazolam with formulations is as follows:

| | | % Decomposition Upon Storage at 25° C. | |
|---|---|---|---|
| Storage Time | Pure drug | Ca-Lactate Base HFC's | Ca-CMC Base HFC's |
| 3 months | 0.255 | 0.14 | 0.15 |
| 6 months | 0.435 | 0.28 | 0.285 |
| 12 months | 0.57 | 0.68 | 0.50 | in which
 Ca-Lactate is calcium lactate
 Ca-CMC is calcium carboxymethyl cellulose
 HFC is hard-filled capsules

DESCRIPTION OF THE PREFERRED EMBODIMENT

Since the calcium carboxymethylcellulose shows faster disintegration and dissolution rate, the formulation using calcium carboxymethylcellulose is preferred over the calcium lactate formulation.

Ketazolam is a tranquilizing agent which has few side effects in man and works in the prescribed once-a-day dosages. The drug is also useful in the treatment of alcoholism.

The following examples are illustrative of the products of the present invention but are not to be construed as limiting.

EXAMPLE 1

One thousand capsules, size #4, each containing 15 mg of ketazolam, are prepared by filling such capsules with a finely-ground mixture of

| Ketazolam | 15 g |
|---|---|
| Calcium lactate | 168 g |
| Sterotex ® | 5 g |

Alternatively, one thousand capsules containing 15 mg of ketazolam each per capsule are prepared by filling one thousand #3 size capsules each with a finely-ground mixture of

| Ketazolam | 15 g |
|---|---|
| Calcium carboxymethylcellulose | 151 g |
| Sterotex ® | 8.75 g |

EXAMPLE 2

For larger amounts of bioavailable ketazolam, capsules of size #4 containing 30 mg of ketazolam each are prepared as follows: per one thousand capsules, a mixture of

| Ketazolam | 30 g |
|---|---|
| Calcium lactate | 120 g |
| Sterotex ® | 5 g | or size #3 capsules (one thousand) as follows:

| Ketazolam | 30 g |
|---|---|
| Calcium carboxymethylcellulose | 145 g |
| Sterotex ® | 9.25 g |

EXAMPLE 3

One thousand hard-filled capsules containing 45 mg of ketazolam per capsule are prepared by admixing the following for capsules #3

| Ketazolam | 45 g |
|---|---|
| Calcium lactate | 135 g |
| Sterotex ® | 6 g | or for a capsule #1

| Ketazolam | 45 g |
|---|---|
| Calcium carboxymethylcellulose | 249 g |
| Sterotex ® | 15.5 g |

EXAMPLE 4

One thousand capsules containing 60 mg of ketazolam per capsule size #2 are prepared by admixing

| Ketazolam | 60 g |
|---|---|
| Calcium lactate | 214 g |

-continued

| | |
|---|---|
| Sterotex ® | 8 g |

EXAMPLE 5

One thousand capsules containing 100 mg of ketazolam per capsule (size #0) are prepared by admixing

| | |
|---|---|
| Ketazolam | 100 g |
| Calcium lactate | 400 g |
| Sterotex ® | 16 g |

The powdered, edible vegetable oil required for these formulations serves as a lubricant and should be neutral, low in ash content, and without metal contamination. Practical examples for such products are Sterotex ® and Sterotex ® HM. Sterotex ® is defined as a vegetable oil product with a melting point of 60°–63° C. and little impurity (heavy metals 10 ppm); Sterotex ® HM melting point between 66.5° and 69.5° C. Both Sterotex ® products are obtained with less than 0.4% acid value, 0.1% moisture and volatiles, and 95% through a screen of 325 mesh. The bulk density (packed) in lb/cft. is 35 for Sterotex ® and 30 for Sterotex ® HM. Sterotex ® products are from Capital City Product Co., Columbus, Ohio.

We claim:
1. A stable solid oral pharmaceutical composition in capsulated unit dosage form useful for combating anxiety which comprises:
    (1) an amount of ketazolam effective for combating anxiety in a patient to whom said composition is administered; and
    (2) powdered, edible vegetable oil, characterized as follows:
        (a) said oil is neutral, exhibiting an acid value of less than 0.4 percent;
        (b) said oil is low in ash content;
        (c) said oil is without metal contamination;
        (d) said oil contains less than 0.1 percent moisture and other volatiles; and
        (e) said oil will pass through a screen of 325 mesh to the extent of about 95 percent.
2. A composition according to claim 1, further comprising:
    (3) calcium lactate.
3. A composition according to claim 1, further comprising:
    (3) calcium carboxymethylcellulose.
4. A composition according to claim 1, further comprising:
    (3) calcium lactate or calcium carboxymethylcellulose.

* * * * *

UNITED STATES PATENT OFFICE
CERTIFICATE OF CORRECTION

Patent No. 4,215,117    Dated 29 July 1980

Inventor(s) Ashok C. Shah; Edward P. Strzelinski

It is certified that error appears in the above-identified patent and that said Letters Patent are hereby corrected as shown below:

Column 1, lines 17-28, the formula appearing therein should read as follows instead of as appears in the printed patent:

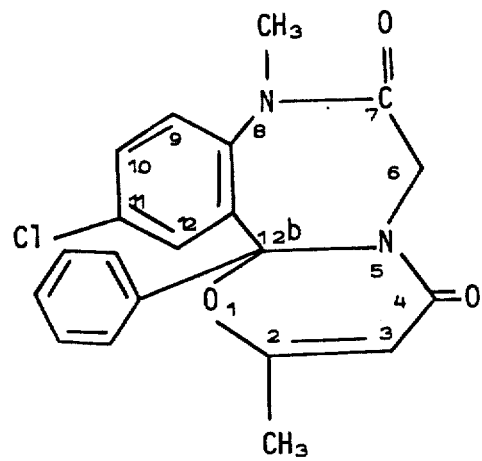

Signed and Sealed this

Twenty-first Day of April 1981

[SEAL]

Attest:

RENE D. TEGTMEYER

Attesting Officer    Acting Commissioner of Patents and Trademarks